US007009700B2

(12) United States Patent
Dubois et al.

(10) Patent No.: US 7,009,700 B2
(45) Date of Patent: Mar. 7, 2006

(54) METHOD AND DEVICE FOR OBTAINING A SAMPLE WITH THREE-DIMENSIONAL MICROSCOPY

(75) Inventors: Frank Dubois, Brussels (BE); Catherine Yourassowski, Brussels (BE)

(73) Assignee: Universite Libre De Bruxelles, Brussels (BE)

( * ) Notice: Subject to any disclaimer, the term of this patent is extended or adjusted under 35 U.S.C. 154(b) by 0 days.

(21) Appl. No.: 10/742,054

(22) Filed: Dec. 18, 2003

(65) Prior Publication Data
US 2004/0156098 A1  Aug. 12, 2004

Related U.S. Application Data

(63) Continuation of application No. PCT/BE02/00111, filed on Jul. 1, 2002.

(30) Foreign Application Priority Data
Jun. 29, 2001 (EP) .................................. 01870147
Dec. 18, 2001 (EP) .................................. 01870281

(51) Int. Cl.
*G01J 3/30* (2006.01)
*G03H 1/26* (2006.01)
(52) U.S. Cl. ........................................ 356/317; 359/22
(58) Field of Classification Search ........ 356/450–456, 356/479, 497, 511, 317, 318, 417, 73, 948, 356/311; 250/458.1, 459.1, 461.1, 461.2; 359/22, 23
See application file for complete search history.

(56) References Cited

U.S. PATENT DOCUMENTS 2,770,166 A   11/1956  Gabor
3,867,009 A   2/1975   Pawluczyk
4,827,125 A   5/1989   Goldstein
5,365,354 A * 11/1994  Jannson et al. ............... 359/15
6,038,041 A   3/2000   Poon et al.
6,496,267 B1 * 12/2002  Takaoka ..................... 356/497

FOREIGN PATENT DOCUMENTS

WO     WO 98/13715     4/1998
WO     WO 00/20929     4/2000

OTHER PUBLICATIONS

F. Dubois, L. Joannes, and J. Legros, "Improved three-dimensional imaging with a digital holography microscope with a source of partial spatial coherence," Applied Optics vol. 38, No. 34 ,pp. 7085-7094 (1999).*

(Continued)

*Primary Examiner*—Andrew H. Lee
(74) *Attorney, Agent, or Firm*—Knobbe Martens Olson & Bear LLP

(57) ABSTRACT

A method and device for obtaining a sample with three-dimensional microscopy, in particular a thick biological sample and the fluorescence field emitted by the sample. One embodiment includes obtaining interferometric signals of a specimen, obtaining fluorescence signals emanating from the specimen, recording these signals, and processing these signals so as to reconstruct three-dimensional images of the specimen and of the field of fluorescence emitted by the specimen at a given time. Another embodiment includes a digital holography microscope, a fluorescence excitation source illuminating a specimen, where the microscope and the fluorescence excitation source cooperate to obtain interferometric signals of the specimen and obtain fluorescence signals emanating from the specimen, means for recording the interferometric signals and fluorescence signals, and means for processing the interferometric signals and the fluorescence signals so as to reconstruct three-dimensional images of the specimen and of the field of fluorescence emitted by the specimen at a given time.

28 Claims, 3 Drawing Sheets

OTHER PUBLICATIONS

Dubois et al., "Improved three-dimensional imaging with a digital holography microscope with a source of partial spatial coherence," *Applied Optics*, vol. 38, No. 34, pp. 7085-7094, Dec. 1999.

* cited by examiner

US 7,009,700 B2

METHOD AND DEVICE FOR OBTAINING A SAMPLE WITH THREE-DIMENSIONAL MICROSCOPY

RELATED APPLICATIONS

This application is a continuation application under 35 U.S.C. § 120 of WO 03/002972, filed as Patent Cooperation Treaty/BE02/00111 on Jul. 1, 2002, which is hereby incorporated by reference.

BACKGROUND

1. Field of the Invention

Aspects of the present invention relate to a method and to an instrument for obtaining three-dimensional images of a specimen by microscopy and for obtaining, in three dimensions, the field of fluorescence emitted by this specimen, said specimen being either fluorescent or prelabeled using one or more fluorochromes.

One of the applications of said method and of said instrument relates more particularly to obtaining three-dimensional images of the fluorescence emitted by biological specimens, that may be thick, for the purpose of observing their dynamic behavior and their change over time.

2. Description of the Related Technology

Conventional fluorescence microscopy has provided substantial progress in the field of biology. In particular, the technique of immunofluorescence has made it possible to carry out specific labeling of molecules and their location in tissues. Moreover, the discovery of GFPs (green fluorescent proteins) has revolutionized the study of locating proteins in living cells and of determining the dynamics and interactions of said proteins.

However, one of the problems encountered in conventional fluorescence microscopy is that of the fluorescence emitted by elements lying outside the plane of sharpness. This parasitic light prevents good acquisition of the image by adding substantial background noise. The images become very difficult to interpret when thick biological specimens, such as embryons, are observed.

Confocal microscopy allows this problem to be overcome by exciting the fluorescence of the specimen over a very small area that scans the specimen and by blocking the fluorescence emitted outside the illuminated area by means of a small aperture.

However, confocal microscopy also has its own drawbacks.

One drawback of confocal microscopy is that this technique requires complete scanning of the specimen by an optomechanical device. This operation requires a relatively long time (typically of the order of a few seconds) to analyze a volume before the image is available to be displayed.

Furthermore, the exciting source used in confocal microscopy is generally an argon or argon-krypton laser that may damage biological specimens.

Another drawback is that the exciting sources do not allow the entire wavelength range needed for observation in fluorescence to be easily covered.

Finally, confocal microscopy is an extremely sophisticated technique that requires great precision during manipulation and is also expensive.

SUMMARY OF THE INVENTION

Certain embodiments of the present invention relate to a method and to an instrument for obtaining three-dimensional images of a specimen, preferably a thick biological specimen, and to obtain, in three dimensions, the field of fluorescence emitted by said specimen, by coupling interferometric signals obtained by digital holography with fluorescence signals.

The term "thick specimen" is understood to mean a specimen whose dimensions are such that it is impossible to have a sharp image simultaneously over the entire depth of the specimen using a conventional optical microscopy method.

In one embodiment of the present invention there is a method of obtaining, by digital holography microscopy, three-dimensional images of a specimen and of a field of fluorescence emitted by the specimen, the method comprising a) obtaining interferometric signals of a specimen, b) obtaining fluorescence signals emanating from the specimen, c) recording the interferometric signals and fluorescence signals, and d) processing the interferometric signals and the fluorescence signals so as to reconstruct three-dimensional images of the specimen and of the field of fluorescence emitted by the specimen at a given time. A) to d) may be repeated over a time period so as to monitor a change in the three-dimensional images of the specimen and of the fluorescence field of the specimen.

The processing may comprise combining the interferometric signals and the fluorescence signals. The specimen may be a thick biological specimen. The processing of the interferometric signals with the fluorescence signals may comprise at least one numerical analysis technique. Recording the interferometric signals and fluorescence signals may include recording the interferometric signals and fluorescence signals sequentially and independently.

In another embodiment of the present invention there is a system for obtaining three-dimensional images of a specimen and of a field of fluorescence emitted by the specimen, the system comprising a digital holography microscope, a fluorescence excitation source illuminating a specimen, wherein the microscope and the fluorescence excitation source cooperate to obtain interferometric signals of the specimen and obtain fluorescence signals emanating from the specimen, means for recording the interferometric signals and fluorescence signals, and means for processing the interferometric signals and the fluorescence signals so as to reconstruct three-dimensional images of the specimen and of the field of fluorescence emitted by the specimen at a given time. The fluorescence excitation source may operate in reflection mode or transmission mode.

The digital holography microscope may comprise a partially coherent, or optionally coherent, light source configured to generate a light beam. The partially coherent light source of the microscope may comprise a source (S) emitting light of small spectral width, a first lens (L1), a first aperture (A1), a second lens (L2), a second aperture (A2) and a third lens (L3), wherein a relative arrangement of these various elements being such that, during operation, the light emitted by the light-emitting source encounters, in succession, the first lens (L1), the first aperture (A1), the second lens (L2), the second aperture (A2) and the third lens (L3), and wherein the light at the exit of the third lens is a collimated light. Alternatively, the partially coherent light source of the microscope may comprise a source (S) emitting light of small spectral width, an optical fiber, a first lens (L1), a second lens (L2), a third lens (L3) and an adjustable aperture (A1), wherein a relative arrangement of these various elements being such that, during operation, the light emitted by the light-emitting source passes firstly through the optical fiber so as to have a homogeneous light field and then encounters the first lens (L1), then the second lens (L2) and the third lens (L3) in order to obtain collimated light at the aperture (A1). Alternatively, the partially coherent light source of the microscope may comprise a laser source (S), a first lens (L1), a rotating diffuser (D), a second lens (L2) and an aperture (A), wherein a relative arrangement of these various elements being such that, during operation, the laser beam emitted by the laser source firstly encounters the first lens (L1), then the rotating diffuser (D), which is placed behind the focal point of the first lens (L1), then the second lens (L2), placed at its focal length with respect to the plane of the rotating diffuser (D), and then the aperture (A). Alternatively, the partially coherent light source of the microscope may comprises a laser source (S), a first lens (L1), a rotating diffuser (D), and a second lens (L2), the relative arrangement of these various elements being such that, during operation, the laser beam emitted by the laser source firstly passes through the first lens (L1), then the diffuser (D) and then the second lens (L2), the laser beam at the exit of the first lens (L1) being focused at a focal point located upstream of the diffuser at an adjustable distance (d) from the diffuser (D). The rotating diffuser (D) may comprise a ground glass plate.

The digital holography microscope may further comprise a movable first subassembly (SE1) comprising a beam splitter (BS1) and a mirror (M1) configured to form two parallel beams, an object beam (O) and a reference beam (R), from a source light beam; means (M) for directing the source light beam onto the first subassembly (SE1) at the beam splitter (BS1); a fixed or movable second subassembly (SE2), comprising a beam splitter (BS2) and a mirror (M2), for combining the object beam (O) and the reference beam (R) into a recombined light beam; an object cell (So) placed in the optical path of the object beam (O) between the first subassembly (SE1) and the second subassembly (SE2), wherein the object cell (So) includes a specimen to be studied; a first microscope objective (ML1) located in the optical path of the object beam (O) between the first subassembly (SE1) and the second subassembly (SE2), downstream of the object cell (So); means for optical path compensation located in the optical path of the reference beam (R) between the first subassembly (SE1) and the second subassembly (SE2); a second microscope objective (ML2) located in the optical path of the reference beam (R) between the first subassembly (SE1) and the second subassembly (SE2) downstream of the optical path compensation means; first focusing means (L4) configured to focus the object beam (O) onto the object cell (So); and second focusing means (L5) configured to focus the reference beam (R) onto the optical path compensation means. The directing means (M) may comprise mirrors. The optical path compensation means may comprise a reference cell (Sr) similar to the object cell (So) but not including the specimen to be studied. The optical path compensation means may comprise a transparent material of suitable thickness and suitable composition. The system may additionally comprise additional focusing means (L6) for focusing the recombined light beam onto the means for recording.

The means for recording may comprise a CCD camera coupled to the means for processing. The means for processing may comprise a computer having image analysis means for processing the interferometric signals and the fluorescence signals. The means for recording the interferometric signals and fluorescence signals may record the interferometric signals and fluorescence signals sequentially and independently.

In another embodiment of the present invention there is a digital holography microscope, comprising a partially coherent light source configured to generate a source light beam; a movable first subassembly (SE1) that comprises a beam splitter (BS1) and a mirror (M1), for forming two parallel beams, an object beam (O) and a reference beam (R), from the source light beam; means (M) for directing the source light beam onto the first subassembly (SE1) at the beam splitter (BS1); a fixed or movable second subassembly (SE2) comprising a beam splitter (BS2) and a mirror (M2) so as to combine the object beam (O) and the reference beam (R) into a recombined light beam; an object cell (So) placed in the optical path of the object beam (O) between the first subassembly (SE1 and the second subassembly (SE2), wherein the object cell (So) includes a specimen to be studied; a first microscope objective (ML1) located in the optical path of the object beam (O) between the first subassembly (SE1) and the second subassembly (SE2), downstream of the object cell (So); means for optical path compensation located in the optical path of the reference beam (R) between the first subassembly (SE1) and the second subassembly (SE2); a second microscope objective (ML2) located in the optical path of the reference beam (R) between the first subassembly (SE1) and the second subassembly (SE2) downstream of the optical path compensation means; first focusing means (L4) configured to focus the object beam (O) onto the object cell (So); and second focusing means (L5) configured to focus the reference beam (R) onto the optical path compensation means. The directing means (M) may comprise mirrors. The optical path compensation means may comprise a transparent material of suitable thickness and suitable composition, or a reference cell (Sr) similar to the object cell (So) but not including the specimen to be studied.

The partially coherent light source may comprises a source (S) emitting light of small spectral width, a first lens (L1), a first aperture (A1), a second lens (L2), a second aperture (A2) and a third lens (L3), wherein a relative arrangement of these various elements being such that, during operation, the light emitted by the light-emitting source encounters, in succession, the first lens (L1), the first aperture (A1), the second lens (L2), the second aperture (A2) and the third lens (L3), and wherein the light at the exit of the third lens is collimated light. Alternatively, the partially coherent light source may comprise a source (S) emitting light of small spectral width, an optical fiber, a first lens (L1), a second lens (L2), a third lens (L3) and an adjustable aperture (A1), wherein a relative arrangement of these various elements being such that, during operation, the light emitted by the light-emitting source passes firstly through the optical fiber so as to have a homogeneous light field and then encounters the first lens (L1), then the second lens (L2) and the third lens (L3) in order to obtain collimated light at the aperture (A1). Alternatively, the partially coherent light source of the microscope may comprise a laser source (S), a first lens (L1), a rotating diffuser (D), a second lens (L2) and an aperture (A), wherein a relative arrangement of these various elements being such that, during operation, the laser beam emitted by the laser source firstly passes through the first lens (L1), then the rotating diffuser (D), which is placed behind the focal point of the first lens (L1), then the second lens (L2), placed at its focal length with respect to the plane of the rotating diffuser (D), and then the aperture (A). Alternatively, the partially coherent light source may comprise a laser source (S), a first lens (L1), a rotating diffuser (D), and a second lens (L2), wherein a relative arrangement of these various elements being such that, during operation, the laser beam emitted by the laser source firstly passes through the first lens (L1), then the diffuser (D) and then the second lens (L2), the laser beam at the exit of the first lens (L1) being focused at a focal point located upstream of the diffuser at an adjustable distance (d) from the diffuser (D). The rotating diffuser (D) may comprise a ground glass plate.

In yet another embodiment of the present invention there is a system for obtaining three-dimensional images of a specimen and of a field of fluorescence emitted by the specimen, wherein the system obtains interferometric signals of the specimen, obtains fluorescence signals emanating from the specimen, records the interferometric signals and fluorescence signals and processes the interferometric signals and the fluorescence signals so as to reconstruct three-dimensional images of the specimen and of the field of fluorescence emitted by the specimen at a given time, the system comprising a digital holography microscope, and a fluorescence excitation source illuminating a specimen viewed by the digital holography microscope.

The fluorescence excitation source may operate in reflection mode or transmission mode. The digital holography microscope may comprise a partially coherent, or optionally coherent, light source configured to generate a light beam.

DETAILED DESCRIPTION OF SEVERAL EMBODIMENTS OF THE INVENTION

The following detailed description presents a description of certain specific embodiments of the present invention. However, the present invention may be embodied in a multitude of different ways as defined and covered by the claims. In this description, reference is made to the drawings wherein like parts are designated with like numerals throughout.

One embodiment of the present invention provides a method and an instrument that make it possible to obtain, by microscopy, three-dimensional images of a specimen, in particular a thick biological specimen, and to measure, in three dimensions, the fluorescence emitted thereby, and that do not have the drawbacks of the conventional microscopy techniques, including those of confocal microscopy.

In particular, another embodiment of the present invention provides a method and an instrument that make it possible both to obtain three-dimensional images of the specimen and of the fluorescence field of this specimen, that is to say, to obtain information about the distribution of the fluorescence over the entire volume of the specimen, and optionally to monitor their change over time, and to do so with a minimum time delay between each image acquisition.

Another embodiment of the invention provides a method and a device that do not require excessively complex manipulation and therefore the cost is competitive, especially compared with confocal microscopy.

Light Sources Used for the Digital Holography

Figure 1:
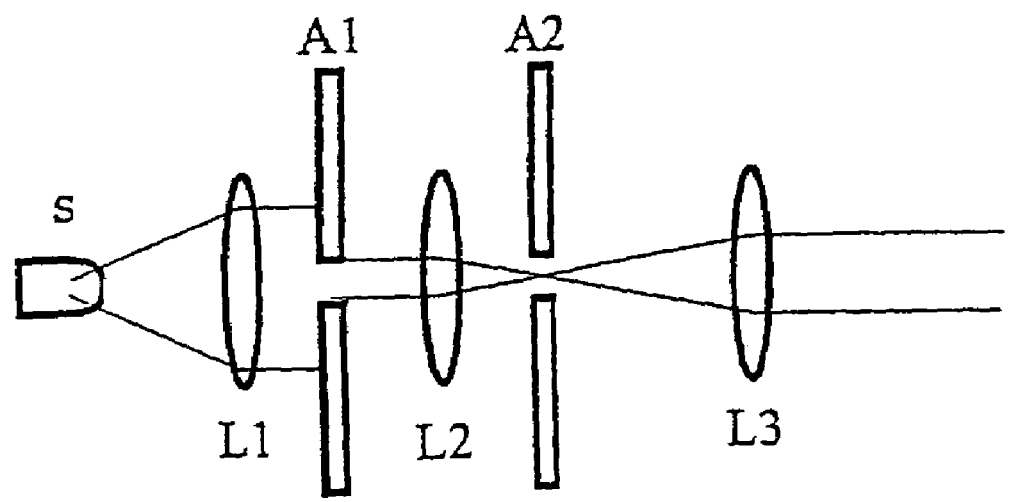
FIG. 1 shows a first embodiment of a spatially partially coherent source according to the present invention, produced from a spatially incoherent source.

A first type of light source that can be used in the instrument according to certain embodiments of the present invention corresponds to a partially coherent source as shown in FIG. 1. An achromatic lens L1 collimates the light rays emitted by an extended spatially incoherent wavelength-filtered source, for example an LED (light-emitting diode) to a first iris diaphragm A1 of adjustable aperture. The aperture A1 limits the angular spectrum of the source so as to increase the spatial coherence of the light. A second achromatic lens L2 creates a secondary source in its focal plane in which a second iris diaphragm A2 limits the size of the source. A third lens L3 forms a collimated beam. For digital holography, the focal lengths of L1, L2, L3 are, for example, 100 mm.

Figure 2:
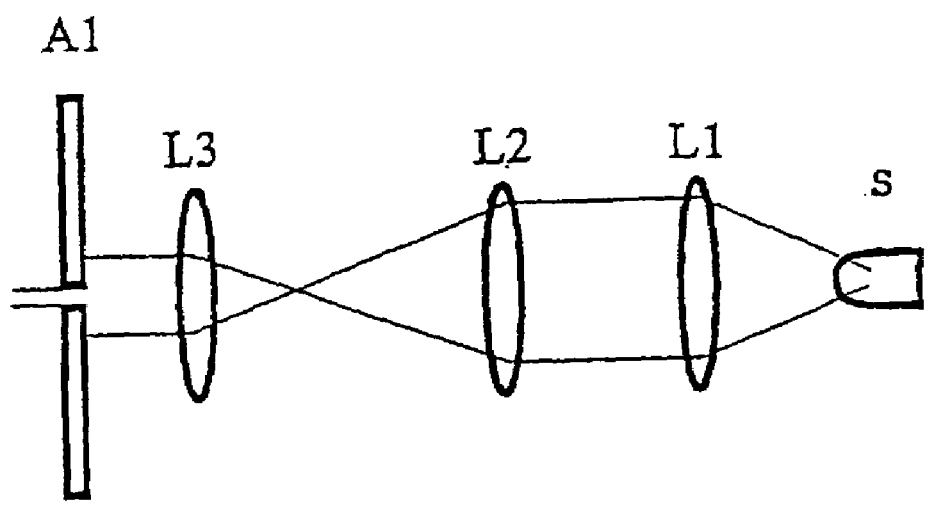
FIG. 2 shows a second embodiment of a spatially partially coherent source according to the present invention, produced from a spatially incoherent source.

A second type of light source that can be used in the instrument according to certain embodiments of the present invention corresponds to a partially coherent source as shown in FIG. 2. A lens L1 collimates the light rays emitted by an extended spatially incoherent wavelength-filtered source, for example an LED (light-emitting diode). To obtain a homogeneous light field, the light rays from this source may be conveyed, from the LED to the lens L1, via an optical fiber whose core is liquid. The set of lenses L2 and L3 forms a collimated beam. The spatial filter A1 limits the angular spectrum of the source so as to increase the spatial coherence of the light.

Figure 3:
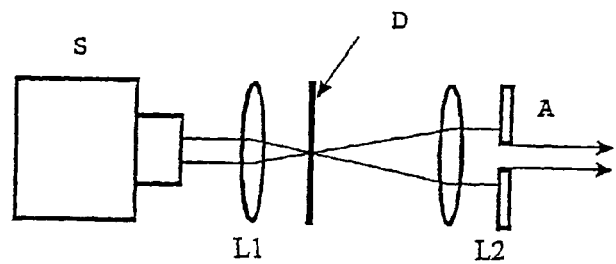
FIG. 3 shows a third embodiment of a spatially partially coherent source according to the present invention, produced from a spatially coherent source.

It is also possible to use in the instrument according to certain embodiments of the present invention a laser source made partially incoherent. FIG. 3 shows the operating principle of such a source conventionally used in optics. A parallel-ray laser beam is focused by a lens L1. A rotating diffuser D is placed behind the focal point so as to form a light spot whose diameter is sufficient to illuminate the field of view of the microscope. The diffuser creates a speckle field that varies with the rotation of the diffuser. A lens L2 is placed so that its focal point lies in the plane of the rotating diffuser.

An aperture A is then placed behind the lens so as to be able to increase the size of the speckle grains. By using a motor rotating sufficiently rapidly compared with the exposure time of the image recording system, it may be shown that such a source is equivalent to a spatially partially coherent source as described above. The width of the spatial coherence is directly related to the size of the speckle grains, which is adjusted by the diameter of the aperture.

Figure 4:
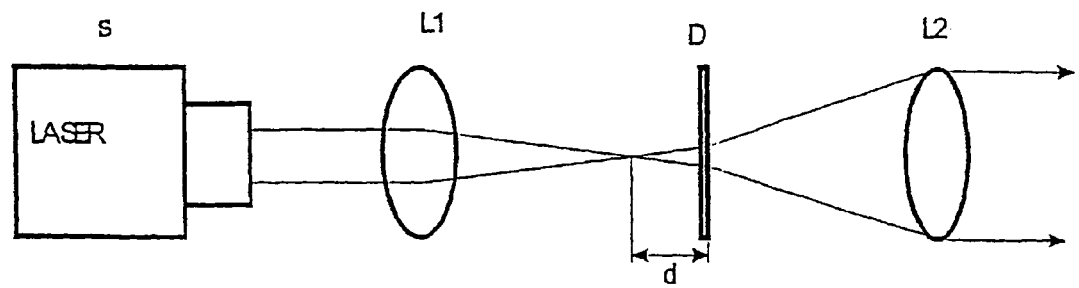
FIG. 4 shows a fourth embodiment of a spatially partially coherent source according to the present invention, produced from a spatially coherent source.

Another type of collimated and partially coherent source based on a coherent source, that can be used in the instrument according to certain embodiments of the present invention, is shown in FIG. 4. A laser beam is focused near a ground glass plate (D) by a lens (L1). The ground glass plate scatters the light. A lens (L2) placed behind the ground glass plate collimates the light scattered by said plate. By adjusting the distance (d) between the focal point and the ground glass plate, the size of the collimated-beam speckle grains is adjusted.

Microscope Operating in Digital Holography

Figure 5:
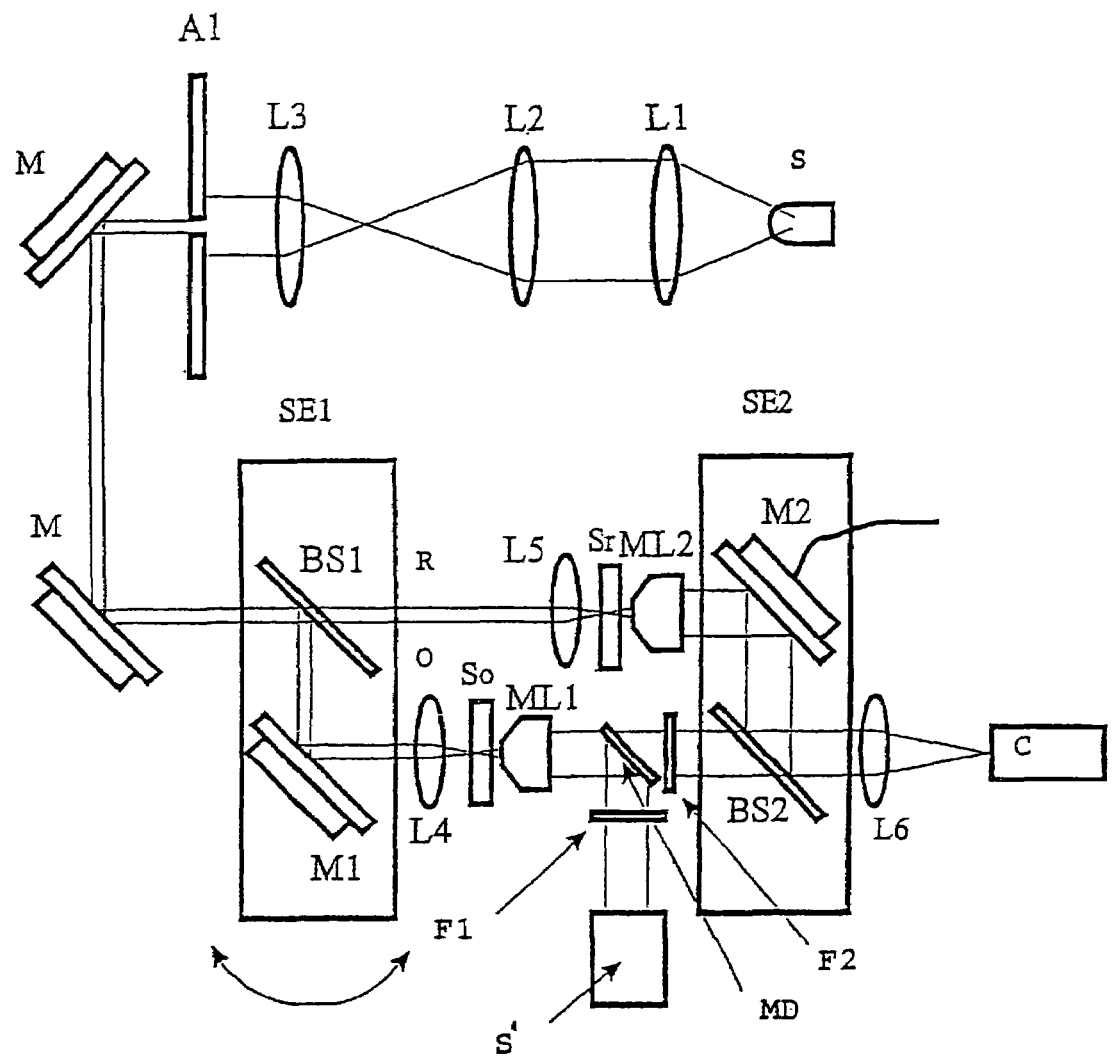
FIG. 5 shows an embodiment of the instrument according to the invention, using a spatially partially coherent source as described in FIG. 2.

FIG. 5 shows the plane of the microscope used in the instrument according to certain embodiments of the present invention. The interferometer of the microscope operating in digital holography is of the Mach-Zehnder type and comprises two subassemblies SE1 and SE2. Each of these has a beam splitter, BS1 and BS2 respectively, and a mirror, M1 and M2 respectively. The source S for the digital holography is a partially coherent source such as one of those described above. Said source S illuminates the beam splitter BS1. One portion of the beam is transmitted by BS1 and one portion is reflected toward the mirror M1.

The first subassembly SE1 is used to form two parallel light beams—the object beam O and the reference beam R. This first subassembly SE1 is mounted on a rotary table, while the second subassembly SE2 is fixed or movable. This makes it possible to adjust the equalization of the optical path of the two beams—the object beam O and the reference beam R—of the interferometer.

As regards the object beam, a lens L4 focuses the light beam onto the object or specimen contained in its observation cell So. The object is observed with a microscope objective ML1 suitable for observing in fluorescence (the various possible magnifications in conventional microscopy can be used). The pair of lenses L4-ML1 forms an afocal system. The objective ML1, in combination with the lens L6, produces the image of a plane passing through the specimen.

Similarly, as regards the reference beam R, the lens L5 focuses the light beam either onto an observation cell Sr, identical to that having the specimen but without the latter being present, or onto a transparent material of suitable composition and thickness, such as for example glass. This arrangement makes it possible to optimize the equalization of the optical path of the two beams of the interferometer.

A microscope objective ML2, identical to ML1, is placed in the reference beam. The pair of lenses L5-ML2 also constitutes an afocal system. The optical paths ML1-L6 and ML2-L6 are adjusted to be identical.

The second subsystem SE2, which comprises the mirror M2 and the beam splitter BS2, is used to combine the object beam O with the reference beam R. The combined object O and reference R beams interfere in the sensitive plane of the camera (labeled C in FIG. 5).

As indicated below, certain embodiments using digital holography may require knowledge of the optical amplitude measured in a plane of sharpness that intercepts the specimen. The optical amplitude may be determined from the interference patterns by two methods:

(i) the carrier or Fourier transform method. Using this method, the object and reference beams are incident on the CCD camera at a small angle so as to obtain, when no specimen is being analyzed, a linear array of interference fringes. The optical phase change introduced by the specimen is then manifested by a variation in the shape of the fringes. The amplitude is determined by Fourier transform analysis;

(ii) the mirror M2 of the subassembly SE2 is provided with a system for piezoelectric displacement along its optical axis, which allows the reference optical path to be changed by precise fractions of a wavelength. This makes it possible to implement what is called the "phase stepping" technique which consists in recording several images phase-shifted by a constant fraction of the wavelength. The combination of these interferograms makes it possible, by computer processing, to calculate the light amplitude emerging from the specimen.

The exemplary microscope can operate in direct or inverse microscopy mode.

Instrument for Fluorescence

In FIG. 5, the fluorescence excitation source S' is placed in reflection mode. As indicated above, it is possible to place this source so as to operate in transmission mode.

Fluorescence in Reflected Light

In this configuration, which corresponds to that shown in FIG. 5; the source S' is either a mercury vapor lamp or a quartz-halogen lamp, or else a source that emits light within a range of short wavelengths that is utilized for fluorescence excitation. Where appropriate, this source may be a laser. The light rays, collimated by a lens, enter an excitation filter F1 selected according to the fluorochrome used and are reflected by a suitable dichroic mirror MD onto the specimen through the objective.

The fluorescent light emitted by the fluorochromes contained in the specimen passes through the dichroic mirror MD, which is transparent at these longer wavelengths, passes through a stop filter F2, placed so as to block any short wavelengths, and is recorded by the camera.

Materials of suitable composition and thickness, for example glass, may be added in the reference beam in order to optimize the equalization of the optical path of the two interferometer beams.

Fluorescence in Transmitted Light

For this configuration, there are two possible constructions:

(i) a single-source construction: the single source used is that provided for the microscope operating in digital holography, but it is used simultaneously as a fluorescence excitation source as it emits in a range of short wavelengths. This makes it possible both to create the hologram of the object and to excite the fluorochromes of the specimen;

(ii) a two-source construction: the source specifically for the microscope operating in digital holography is combined with the source that emits the light needed for exciting the fluorochromes in the two following ways: either the source utilized for the fluorescence is placed just in front of the beam splitter BS1 or this source is placed just in front of the lens L4 that focuses the light rays onto the specimen.

Coupling of the Digital Holography and Fluorescence Signals for the 3D Reconstruction of the Fluorescence Signals As described above, the instrument comprises two coupled optical subsystems for:

(i) recording the interferometric images in transmission of the specimen;

(ii) recording the fluorescence image of the specimen activated by the fluorescence excitation source.

These images are formed by the afocal system consisting of the pair of lenses ML1-L6 that produces the sharp image of a plane perpendicular to the optical axis of the specimen on the sensitive surface of the camera C. The interferometric and fluorescence images are recorded sequentially:

(i) the fluorescence source is masked by a shutter and the interferometric image or images are recorded;

(ii) the source for the interferometric recording is masked or turned off and the fluorescence image or images are recorded.

When the thickness of the specimen is smaller than the depth of field of the imaging device, the image of the specimen is sharp everywhere. However, and it is this case to which the present development relates, when the thickness of the specimen exceeds the depth of field, those parts of the specimen beyond the depth of field region give fuzzy parts in the image.

Since the specimen is observed by a camera C using an afocal lens system ML1-L6, the interferometric and fluorescence signals are perfectly superposed at the sensor and the planes of sharpness are common for both types of illumination thanks to the use of achromatic optical components ML1-L6.

Role of the Interferometric or Holographic Recording

The interferometric recording allows precise measurement of the complex optical amplitude in the sharp plane of the specimen. The coherent or partially coherent interferometric source S is activated and illuminates, as a collimated beam, the beam splitter BS1.

One portion of this beam, called the object beam, follows the path BS1-M1-L4-So-ML1-BS2-L6-C. The phase and the amplitude of this beam are modulated by the specimen contained in the object cell So.

The other portion of the beam, called the reference beam, follows the path BS1-L5-Sr-ML2-M2-BS2-L6-C. The phase and the amplitude of this beam are modulated by the reference cell Sr.

The object and reference beams interfere on the sensitive surface of the camera C. The shape of the interference pattern is influenced by the relative optical phase changes introduced by the specimens So and Sr. Since the reference cell Sr is an experimental cell similar to the object cell So, but without the specimen under investigation, the shape of the interference pattern is significantly influenced only by the optical phase changes introduced by the specimen under investigation.

The first objective is to measure the emergent complex optical amplitude from the specimen on the basis of the interference pattern or patterns measured by the camera. To do this, two methods conventional in interferometry are available:

(i) the Fourier transform method [1];
(ii) the phase shift method.

Knowing the complex optical amplitude in the plane of sharpness of the specimen, digital holography methods are used to calculate the complex amplitudes in parallel planes [2–6]. These methods consist in calculating, by numerical methods, the optical field using the Fourier optics propagation laws (Kirchhoff-Fresnel equation). It is thus possible to calculate the complex light amplitudes in planes that are away from the initial depth of field region of the imaging system. Thus, those image regions that were recorded fuzzy are made sharp by using these methods.

A complex optical amplitude $u(x,y)$ in an $(x,y)$ plane is given by:

$$u(x, y) = \sqrt{I(x,y)} \exp\{i\alpha(x, y)\} \quad (1)$$

where: $I(x,y)$ is the light intensity at the point $(x,y)$;
$\alpha(x,y)$ is the optical phase at the point $(x,y)$; and
$i$ is the imaginary number such that $i^2 = -1$.

The interferometric method therefore amounts to determining, in the plane in which the image is produced, the quantities $I(x,y)$ and $\alpha(x,y)$ so as to be able to calculate, by digital holography, the optical amplitude $u_d'(x',y')$ in the parallel planes separated by distances d. This operation is formally written as:

$$u_d'(x', y') = R[d]u(x, y) \quad (2)$$

where: $R[d]$ is the Kirchhoff-Fresnel operator.

Several numerical evaluations of this expression exist in the literature [2].

Recording of the Fluorescence Signal

When the fluorescence excitation source is activated, the fluorescent substances distributed within the specimen emit light isotropically, giving rise to a signal detected by the CCD video camera. If we consider the emission by a point $(x0,y0)$ of the specimen located at a distance d from the plane, the image of which is formed by the lens pair ML1-L6, owing to the fact that the objective of the microscope has a finite aperture, the fluorescence-emitting point produces, in the plane of the object whose image is formed, a light disk that can be observed by the video camera.

This distribution of the light intensity is denoted by $I_p(x-x0, y-y0)$ where the subscript p indicates that it is the fluorescence signal that is considered.

The diameter D of the luminous disk is given, to a first approximation, by:

$$D = \frac{d}{fnumber_{ML1}} \quad (3)$$

where $fnumber_{ML1}$ is the ratio of the focal length of ML1 to the diameter of its aperture.

It should be noted that equation (3) is corrected for the very short distances d with which the diffraction effects in incoherent illumination have to be considered. However, for these distances d, the image of the point source lies in the depth of field region and therefore requires no subsequent manipulation as regards sharpness.

In the case of more complex specimens, having several emission regions that may be located at different distances d from the plane of sharpness, a light intensity distribution is obtained that is expressed as the sum of elementary contributions: $I_p(x-x0,y-y0)$.

Coupling Between the Complex Amplitude of the Digital Holography Signal and the Fluorescence Signal The concept forming the subject-matter of the present patent application is the coupling between the digital holography signal and the fluorescence signal so as to be able to manipulate the fluorescence signal and be able to sharpen, by a digital holography numerical process, fluorescence signals that have been recorded fuzzy.

To be able to accomplish this coupling, it is necessary for the regions within the biological specimen that exhibit fluorescence to have optical properties (optical absorbence and/or refractive index) that are different from the nonfluorescent regions that surround them. It should be pointed out that this condition is satisfied in many applications in cell biology, since fluorescence is used for labeling cell organelles that are also visible by optical microscopy in phase contrast. This demonstration by phase contrast reveals a local variation in refractive index and/or of absorbence of the organelles.

If we consider a limited region of fluorescence within the biological specimen that is also a region in which there is a local index and/or absorbence change relative to a constant background and if it is assumed that this region lies at a distance d from the plane of sharpness of the specimen, the fluorescence region, as described above, gives rise to a light spot of intensity $I_p(x-x0,y-y0)$. The light amplitude measured by interferometry is given by equation (1):

$$u(x, y) = \sqrt{I(x,y)} \exp\{i\alpha(x, y)\}.$$

Firstly, an equivalent fluorescence amplitude is constructed by:

$$u_p(x, y) = A\sqrt{I_p(x - x0, y - y0)} \sqrt{I(x, y)} \exp\{i\alpha(x, y)\} \quad (4)$$

where A is a multiplicative constant that does not play a key role in the present discussion.

Equation (4) weights the interferometric amplitude by the intensity of fluorescence so as to amplify the fluorescence-influenced region.

Next, digital holography reconstruction is applied in order to reconstruct the sharp image of the fluorescence:

$$u_p'(x', y') = R[-d]u_p(x, y) \quad (5)$$

Next, the light intensity $u_p'^*(x',y')u_p'(x',y')$ is then calculated in order to obtain the sharp image of intensity of the fluorescence spot.

In practice, the interferometric light amplitude and the fluorescent light spot are measured without knowing the distance d. The digital holography reconstruction technique is then applied incrementally in order to achieve the sharpest image of the fluorescence spot.

If we now consider the case in which, within the specimen, there are several limited regions with refractive index and/or absorbence variations, among which only some of these regions exhibit fluorescence emission, two cases may arise:

(i) 1st case: the interferometry and fluorescence signals are separate in the sharp plane of the specimen. In this case, the method as described above may be used directly;

(ii) 2nd case: the interferometry and fluorescence signals overlap, at least partially, in the sharp plane of the specimen.

In this second case, the use of the method as described above may give rise to false reconstructions of the fluorescent regions, which are in fact not so. This is because, if we consider, on the one hand, the interferometry signals due to two regions of index and/or absorbence variations that are superposed and, on the other hand, that only one of these two regions exhibits fluorescence, since the fluorescence spot at least partially overlaps the interferometric signals emanating from the two regions, the use of the above method will give a significant contribution to the fluorescence for the two regions. In this case, many correction methods may be implemented so as to reconstruct only the relevant region. Mention may be made, by way of example, of an iterative correction procedure. The initial fluorescence distribution in the plane of sharpness will be called D0. At the first iteration, the above holographic reconstruction method is used, which gives fluorescence contributions for both regions. The result of this reconstruction will be called the configuration C1. Next, using the propagation laws of incoherent optics, the fluorescent light distribution, called D1, in the plane of sharpness of the specimen, which corresponds to C1, is calculated. D1 and D0 are compared so as to apply a correction to C1 and obtain a second configuration C2. From this, a new fluorescence distribution D2 is calculated by the laws of incoherent optics and the iterative correction process is thus repeated until a sufficiently small difference is obtained between the fluorescence distribution DN (Nth iteration) calculated by the laws of incoherent optics and the fluorescence distribution D0. Many numerical optimization methods may be used to implement such an optimization procedure. By way of example, mention may be made of the simulated annealing methods based on random searching for the minimization of a cost function, which in the present case could be $(DN-D0)^2$ [7].

To summarize, certain embodiments of the present invention consist in combining a fluorescence instrument with a microscope operating in digital holography in order to measure, in three dimensions, fluorescent regions of microspecimens, and offers many advantages over the currently known techniques.

A first advantage is that certain embodiments of the present invention, compared with conventional fluorescence microscopy, allow a three-dimensional image of the fluorescence to be obtained without it being necessary to move the specimen along the optical axis of the system.

Furthermore, in certain embodiments of the present invention, the phase and amplitude information provided by the digital holography may be used to remove, at each point, the parasitic fluorescence by digital processing.

Compared with confocal microscopy, certain embodiments of the present invention also have particular advantages.

One of these advantages is that certain embodiments of the invention are much less complex to implement than confocal microscopy.

Another advantage, in certain embodiments, is that it makes it possible to use an extended range of light sources to generate the fluorescence signal, and it therefore extends the wavelength range available to cover the applications. This also allows the use of sources that are less aggressive to biological specimens.

It should also be noted that, compared with confocal microscopy, certain embodiments of the present invention allow information to be recorded about the entire specimen simultaneously over the volume and with a very small time delay between each acquisition (typically 1/25 s) for recording the fluorescence, in such a way that the temporal distortion introduced by the scanning in confocal microscopy is eliminated.

In conclusion, the method proposed in certain embodiments of the present invention, which consists in coupling interferometry signals with fluorescence signals, makes it possible to locate, in three dimensions, and with sharp images, the regions that exhibit fluorescence within a specimen. This method is applicable in the field of embryology in which biologists wish to examine the change in and dynamics of living embryons which very rapidly exhibit thicknesses that exceed the depth of field of optical microscopes. Thus, certain embodiments of the present invention may allow, for example, a posteriori three-dimensional analysis of the movement of cells labeled by fluorochromes.

Furthermore, the holographic microscope according to certain embodiments of the present invention also has a number of advantages over the instruments of the prior art, in particular compared with the holographic microscope described in the article "Improved three-dimensional imaging with digital holography microscope using a partial spatial coherent source" by F. Dubois et al., *Appl. Opt.* 38, pp. 7085–7094 (1999).

CONCLUSION

Specific blocks, sections, devices, functions and modules may have been set forth. However, a skilled technologist will realize that there are many ways to partition the system of the present invention, and that there are many parts, components, modules or functions that may be substituted for those listed above.

While the above detailed description has shown, described, and pointed out the fundamental novel features of the invention as applied to various embodiments, it will be understood that various omissions and substitutions and changes in the form and details of the system illustrated may be made by those skilled in the art, without departing from the intent of the invention.

Literature References

1. M. Takeda, H. Ina and S. Kobayashi, "Fourier transform method of fringe pattern analysis for computer based topography and interferometry", J. Opt. Soc. Am. 72, 156–160 (1972).
2. F. Dubois, L. Joannes and J.-C. Legros, "Improved three-dimensional imaging with digital holography microscope using a partial spatial coherent source", Appl. Opt. 38, 7085–7094 (1999).
3. E. Cuche, F. Bevilacqua and C. Depeursinge, "Digital holography for quantitative phase contrast imaging", Opt. Let. 24, 291–293 (1999).
4. T. Zhang and I. Yamaguchi, "Three-dimensional microscopy with phase-shifting digital holography", Opt. Let. 23, 1221–1223 (1998).
5. Skarman, Wozniac and Becker, "Simultaneous 3D-PIV and temperature measurement using a New CCD based holographic interferometer", Flow Meas. Instr. 7, No. 1, pp. 1–6 (1996).
6. Y. Takaki and H. Ohzu, "Hybrid holographic microscopy: Visualization of three-dimensional object information by use of viewing angles", Appl. Opt. 39, 5302–5308 (2000).
7. S. Kirkpatrick, C. D. Gelatt, Jr. and M. P. Vecchi, "Optimization by Simulated Annealing", Sciences 220, 671–679 (1983).
8. B. W. Schilling, T.-C. Poon, G. Indebetouw, B. Storrie, K. Shinoda, Y. Suzuki and M. H. Wu, "Three-dimensional holographic fluorescence microscopy", Optics Letters 22, No. 19, 1506–1508 (1997).

What is claimed is:

1. A method of obtaining three-dimensional images of a specimen and of a field of fluorescence emitted by the specimen, the method comprising, with a system able to operate in digital holography microscopy:
   a) obtaining simultaneously in one step all the digital holographic information of the entire volume of the specimen;
   b) obtaining simultaneously in one step all the fluorescence signals emanating from the entire volume of the specimen;
   c) recording all the digital holographic information and all the fluorescence signals emanating from the entire volume of the specimen;
   d) processing all the digital holographic information so as to reconstruct a three-dimensional image of the entire volume of the specimen at a given time; and
   e) processing all the fluorescence signals so as to reconstruct a three-dimensional image of the field of fluorescence emitted by the entire volume of the specimen at a given time, said processing including combining all the fluorescence signals with all the digital holographic information.

2. The method as claimed in claim 1, wherein the specimen is a thick biological specimen.

3. The method as claimed in claim 1, wherein a) to e) are repeated over a time period.

4. The method as claimed in claim 1, wherein the processing at d) comprises performing a Fourier transform method or a phase-stepping method.

5. The method as claimed in claim 1, wherein in c) the recording of all the digital holographic information and the recording of all the fluorescence signals are performed separately and independently.

6. A system for obtaining three-dimensional images of a specimen and of a field of fluorescence of the specimen, wherein
   the system obtains simultaneously in one step all the digital holographic information of the entire volume of the specimen, the system obtains simultaneously in one step all the fluorescence signals emanating from the entire volume of the specimen, the system records all the digital holographic information and all the fluorescence signals, the system processes all the digital holographic information so as to reconstruct a three-dimensional image of the entire volume of the specimen at a given time, the system processes all the fluorescence signals, including combining all the fluorescence signals with all the digital holographic information, so as to reconstruct a three-dimensional image of the field of fluorescence emitted by the entire volume of the specimen at a given time, wherein the system comprises:
   a digital holographic microscope configured to obtain the digital holographic information and the fluorescence signals of the specimen;
   a fluorescence excitation source configured to illuminate the specimen;
   recording means configured to record the digital holographic information and the fluorescence signals; and
   processing means configured to process the digital holographic information and the fluorescence signals.

7. The system as claimed in claim 6, wherein the fluorescence excitation source operates in reflection mode or in transmission mode.

8. The system as claimed in claim 6, wherein the digital holographic microscope comprises a light source for illuminating the specimen, said light source being spatially partially coherent or spatially coherent.

9. The system as claimed in claim 8, wherein the spatially partially coherent light source of the microscope comprises: a source (S) emitting light of small spectral width, a first lens (L1), a first aperture (A1), a second lens (L2), a second aperture (A2) and a third lens (L3), wherein a relative arrangement of these various elements being such that, during operation, the light emitted by the light-emitting source encounters, in succession, the first lens (L1), the first aperture (A1), the second lens (L2), the second aperture (A2) and the third lens (L3), and wherein the light at the exit of the third lens is a collimated light.

10. The system as claimed in claim 8, wherein the spatially partially coherent light source of the microscope comprises: a source (S) emitting light of small spectral width, an optical fiber, a first lens (L1), a second lens (L2), a third lens (L3) and an adjustable aperture (A1), wherein a relative arrangement of these various elements being such that, during operation, the light emitted by the light-emitting source passes firstly through the optical fiber so as to have a homogeneous light field and then encounters the first lens (L1), then the second lens (L2) and the third lens (L3) in order to obtain collimated light at the aperture (A1).

11. The system as claimed in claim 8, wherein the spatially partially coherent light source of the microscope comprises: a laser source (S), a first lens (L1), a rotating diffuser (D), a second lens (L2) and an aperture (A), wherein a relative arrangement of these various elements being such that, during operation, the laser beam emitted by the laser source firstly encounters the first lens (L1), then the rotating diffuser (D), which is placed behind the focal point of the first lens (L1), then the second lens (L2), placed at its focal length with respect to the plane of the rotating diffuser (D), and then the aperture (A).

12. The system as claimed in claim 8, wherein the spatially partially coherent light source of the microscope comprises: a laser source (S), a first lens (L1), a rotating diffuser (D), and a second lens (L2), the relative arrangement of these various elements being such that, during operation, the laser beam emitted by the laser source firstly passes through the first lens (L1), then the diffuser (D) and then the second lens (L2), the laser beam at the exit of the first lens (L1) being focused at a focal point located upstream of the diffuser at an adjustable distance (d) from the diffuser (D).

13. The system as claimed in claim 12, wherein the rotating diffuser (D) comprises a ground glass plate.

14. The system as claimed in claim 6, wherein the digital holographic microscope further comprises:
- a movable first subassembly (SE1) comprising a beam splitter (BS1) and a mirror (M1) configured to form two parallel beams, an object beam (O) and a reference beam (R), from a source light beam;
- means (M) for directing the source light beam onto the first subassembly (SE1) at the beam splitter (BS1);
- a fixed or movable second subassembly (SE2), comprising a beam splitter (BS2) and a mirror (M2), for combining the object beam (O) and the reference beam (R) into a recombined light beam;
- an object cell (So) placed in the optical path of the object beam (O) between the first subassembly (SE1) and the second subassembly (SE2), wherein the object cell (So) includes a specimen to be studied;
- a first microscope objective (ML1) located in the optical path of the object beam (O) between the first subassembly (SE1) and the second subassembly (SE2), downstream of the object cell (So);
- means for optical path compensation located in the optical path of the reference beam (R) between the first subassembly (SE1) and the second subassembly (SE2);
- a second microscope objective (ML2) located in the optical path of the reference beam (R) between the first subassembly (SE1) and the second subassembly (SE2) downstream of the optical path compensation means;
- first focusing means (L4) configured to focus the object beam (O) onto the object cell (So); and
- second focusing means (L5) configured to focus the reference beam (R) onto the optical path compensation means.

15. The system as claimed in claim 14, wherein the directing means (M) comprises mirrors.

16. The system as claimed in claim 14, wherein the optical path compensation means comprises a reference cell (Sr) similar to the object cell (So) but not including the specimen to be studied.

17. The system as claimed in claim 14, wherein the optical path compensation means comprises a transparent material of suitable thickness and suitable composition.

18. The system as claimed in claim 14, additionally comprising additional focusing means (L6) for focusing the recombined light beam onto the recording means.

19. The system as claimed in claim 6, wherein the recording means comprises a CCD camera and the processing means comprises a computer coupled to the CCD camera and having image analysis means.

20. The system as claimed in claim 6, wherein the recording means records the digital holographic information and the fluorescence signals of the specimen sequentially and independently.

21. The method as claimed in claim 3, wherein a) to e) are repeated over a time period so as to monitor a change in the three-dimensional image of the specimen and/or a change in the three-dimensional image of the field of fluorescence of the specimen.

22. The system as claimed in claim 8, wherein the spatially partially coherent or the spatially coherent light source is generated by configuring a light-emitting source.

23. The system as claimed in claim 8, wherein the light source comprises a light-emitting source, said light-emitting source and the fluorescence excitation source being two different sources.

24. The system as claimed in claim 8, wherein the light source comprises a light-emitting source, said light-emitting source and the fluorescence excitation source being the same source.

25. A method of obtaining, by digital holography microscopy, three-dimensional images of a specimen and of a field of fluorescence emitted by the specimen, the method comprising:
a) simultaneously obtaining digital holographic information of the entire volume of the specimen;
b) simultaneously obtaining fluorescence signals emanating from the entire volume of the specimen;
c) recording the digital holographic information and the fluorescence signals;
d) processing the digital holographic information so as to reconstruct a three-dimensional image of the entire volume of the specimen at a given time; and
e) processing the fluorescence signals so as to reconstruct a three-dimensional image of the field of fluorescence emitted by the entire volume of the specimen at a given time, said processing including combining the fluorescence signals with the digital holographic information.

26. A method of obtaining, by digital holography microscopy, three-dimensional images of a specimen and of a field of fluorescence emitted by the specimen, the method comprising:
a) obtaining, in a single step, digital holographic information of an entire specimen;
b) obtaining, in a single step, fluorescence signals emanating from the entire specimen;
c) recording the digital holographic information and fluorescence signals; and
d) processing the digital holographic information and the fluorescence signals so as to reconstruct three-dimensional images of the specimen and of the field of fluorescence emitted by the specimen at a given time, wherein the processing of the fluorescence signals includes combining the fluorescence signals with the digital holographic information.

27. A method of obtaining, by digital holography microscopy, three-dimensional images of a specimen and of a field of fluorescence emitted by the specimen, the method comprising:
a) obtaining, without scanning, digital holographic information of an entire specimen;
b) obtaining, without scanning, fluorescence signals emanating from the entire specimen;
c) recording the digital holographic information and fluorescence signals; and d) processing the digital holographic information and the fluorescence signals so as to reconstruct three-dimensional images of the specimen and of the field of fluorescence emitted by the specimen at a given time, wherein the processing of the fluorescence signals includes combining the fluorescence signals with the digital holographic information.

28. A system for obtaining three-dimensional images of a specimen and of a field of fluorescence of the specimen, wherein the system simultaneously obtains digital holographic information of the entire volume of the specimen, simultaneously obtains fluorescence signals emanating from the entire volume of the specimen, records the digital holographic information and the fluorescence signals, processes the digital holographic information so as to reconstruct a three-dimensional image of the entire volume of the specimen at a given time, and processes the fluorescence signals, including combining the fluorescence signals with the digital holographic information, so as to reconstruct a three-dimensional image of the field of fluorescence emitted by the entire volume of the specimen at a given time, wherein the system comprises:

a digital holographic microscope configured to obtain the digital holographic information and the fluorescence signals of the specimen;

a fluorescence excitation source configured to illuminate the specimen;

recording means configured to record the digital holographic information and the fluorescence signals; and processing means configured to process the digital holographic information and the fluorescence signals.

* * * * *

UNITED STATES PATENT AND TRADEMARK OFFICE
CERTIFICATE OF CORRECTION

| | | |
|---|---|---|
| PATENT NO. | : 7,009,700 B2 | Page 1 of 1 |
| APPLICATION NO. | : 10/742054 | |
| DATED | : March 7, 2006 | |
| INVENTOR(S) | : Dubois et al. | |

It is certified that error appears in the above-identified patent and that said Letters Patent is hereby corrected as shown below:

Title page item [75] delete the inventor's name "Yourassowski" and insert --Yourassowsky-- therefor.

Column 4, line 14, please delete "(SEI" and insert --(SEI) --, therefor.

Signed and Sealed this

Nineteenth Day of December, 2006

JON W. DUDAS
*Director of the United States Patent and Trademark Office*